United States Patent [19]

Kraemer et al.

[11] Patent Number: 4,975,531

[45] Date of Patent: Dec. 4, 1990

[54] SAKYOMICIN E AND THE DERIVATIVES THEREOF, A PROCESS FOR THE PREPARATION THEREOF AND THE USE THEREOF

[75] Inventors: Hans P. Kraemer; Lutz Robbel; Ludger M. Schwenen, all of Marburg, Fed. Rep. of Germany

[73] Assignee: Behringwerke Aktiengesellschaft, Marburg, Fed. Rep. of Germany

[21] Appl. No.: 332,916

[22] Filed: Apr. 4, 1989

[30] Foreign Application Priority Data

Apr. 6, 1988 [DE] Fed. Rep. of Germany ....... 3811463

[51] Int. Cl.$^5$ .................. C07D 309/10; C12P 29/00; A61K 31/71; C09B 3/78
[52] U.S. Cl. .................................. 536/18.1; 536/4.1; 536/122; 514/34; 514/908; 435/105; 435/252.1
[58] Field of Search ....................... 536/4.1, 18.1, 122; 514/34, 908

[56] References Cited

U.S. PATENT DOCUMENTS 4,847,245  7/1989  Jefson et al. ...................... 536/4.1
4,918,171  4/1990  Oshio et al. ...................... 536/4.1

OTHER PUBLICATIONS

"Methods for Characterization of Streptomyces Species", International Journal of Systematic Bacteriology, pp. 330–340, E. B. Shirling et al., vol. 16, No. 3 (1966).

*Primary Examiner*—Ronald W. Griffin
*Attorney, Agent, or Firm*—Finnegan, Henderson, Farabow, Garrett and Dunner

[57] ABSTRACT

The compounds of the formula I

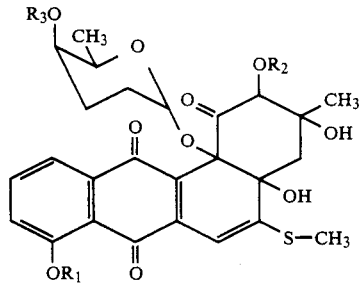

in which $R_1$ to $R_3$ denote, independently of one another, hydrogen or a $(C_1-C_{18})$-acyl group, and a process for the preparation thereof are described. These compounds have tumor-inhibiting properties.

3 Claims, 6 Drawing Sheets

SAKYOMICIN E AND THE DERIVATIVES THEREOF, A PROCESS FOR THE PREPARATION THEREOF AND THE USE THEREOF

The invention relates to sakyomicin E and derivatives of this having the general formula I in which $R_1$-$R_3$ denote, independently of one another, hydrogen or a ($C_1$-$C_{18}$)-acyl group, to a process for the preparation thereof, which comprises Actinomadura spec. being fermented and the compounds of the general formula I being isolated from the culture medium or mycelium and, where appropriate, acylated, and to the use thereof for the preparation of medicinal agents Sakyomicins are prepared by fermentation with a microorganism strain (deposited on Sept. 15, 1987, at the deutsche Sammlung für Mikroorganismen (DSM, German Microorganism Collection), 3300 Braunschweig, Mascheroder Weg 1b, under depository number DSM 4249) which was isolated from a sample of soil from India. The microorganism has been identified as Saccaromonospora spec. formerly tentatively named Actinomadura spec. Sakyomicinones can be obtained from these sakyomicins by acid hydrolysis or methanolysis.

The known sakyomicins and sakyomicinones have antibacterial and tumor-inhibiting effects and can therefore be used in the form of pharmaceutical products for the treatment of infections caused by bacteria or for treatment of oncoses on humans and animals.

The invention is explained hereinafter, especially with its preferred embodiments, and is defined in the patent claims.

The microorganism has the following characteristics:

| | |
|---|---|
| spore surface | smooth |
| spore morphology | RF |
| color of aerial mycelia | white-gray |
| color of substrate mycelia | dark red |

The strain DSM 4249 is used for the fermentation.

Particularly suitable and preferred as carbon source for the aerobic fermentation is glucose, as well as carbohydrate-containing natural products such as malt extract. Suitable and preferred as nitrogen-containing nutrient source are peptone and tryptone, as well as meat extract and yeast extract. The nutrient solution can also contain, for example, chlorides, carbonates or phosphates as additional inorganic salts, or other trace elements.

The concentration of sakyomicin E depends on the conditions of culturing the microorganism. When a nutrient medium which contains soybean peptone (10 g/l), glucose (20 g/l), $CaCO_3$ (2 g/l) and $CoCl_2.6H_2O$ (1 mg/l) at a pH of 7.2 there is formation of about 20% sakyomicin E besides the known sakyomicin A. If the amino acid methionine is added (up to 200 mg/l) to the medium there are formed sakyomicin E and another sakyomicin as main products (80%). It is likewise possible to shift the ratio of amounts of the sakyomicins to the side of sakyomicin E by adding other sulfur-containing amino acids.

The fermentation takes place aerobically, that is to say, for example, submerged with shaking or stirring in shaken flasks or fermenters, where appropriate introducing air or oxygen. The fermentation can preferably be carried out at a temperature of 25° to 30° C. The microorganism is cultivated under the said conditions for about 65 to 70 hours.

The cultivation is advantageously carried out in several stages, i.e. one or more precultures are initially prepared in a liquid nutrient medium and are then transferred into the actual production medium, the main culture, for example in a ratio of 1:14 by volume. The preculture is obtained, for example, by transferring a sporulated aerial mycelium into a nutrient solution and leaving it to grow for about 65-70 hours. The sporulated mycelium can be obtained by leaving the strain to grow for about 10 days on a nutrient medium, for example glucose/yeast extract/malt extract agar.

The progress of the fermentation can monitored by means of the pH and of the $pO_2$ of the culture, or of the mycelium volume, by thin-layer chromatography (TLC) or extraction with subsequent UV measurement at 416 nm or by high-pressure liquid chromatography (HPLC).

Sakyomicin E is isolated from the culture medium by known methods taking account of the chemical, physical and biological properties of the product. It is possible to use TLC, for example on silica gel with chloroform/methanol as mobile phase, to assay the antibiotic concentration in the culture medium or in the individual stages in the isolation, with the amount of antibiotics formed expediently being compared with a calibration solution.

Sakyomicin E is present together with the known sakyomicin A in the mycelium and in the culture filtrate. The antibiotics can be extracted from the unfiltered culture broth using an organic solvent which is immiscible or only slightly miscible with water, such as ethyl acetate or chloroform. However, because only a small proportion of the compounds is present in the mycelium, it is advantageous to separate the culture broth from the mycelium, for example by centrifugation or by filtration, preferably with addition of filtration aids.

It is likewise possible to adsorb sakyomicin E from the culture broth using sorbents (for example $^R$XAD-2 or $^R$XAD-4 from Serva) and subsequently to elute it from the adsorber resin using increasing methanol concentrations.

The antibiotics can then be isolated from the supernatant or filtrate, expediently in the slightly acid to neutral pH range, preferably at pH 6–7. It is expedient to use for this organic solvents which are slightly miscible or immiscible with water, especially ethyl acetate or chlorinated hydrocarbons such as chloroform or methylene chloride. Highly lipophilic concomitants, which may make up a large proportion of the total extract, are removed from the colored extracts, where appropriate after evaporation and taking up in a polar solvent, by precipitation with a non-polar solvent, expediently a hydrocarbon such as n-hexane or a mixture such as petroleum ether. Sakyomicin E can be isolated from the residue by chromatography.

To isolate sakyomicin E from the defatted crude extract, the latter is expediently purified on silica gel (column or preparative TLC), eluents which have proven suitable being a mixture of low molecular weight chlorinated hydrocarbons and alcohols, for example chloroform and methanol in the ratio 9:1 by volume or methylene chloride and ethanol in the ratio 9:1 by volume. The components, which are adsorbed in the form of zones of various colors, are successively eluted in the form of fractions of various colors. The main fraction contains sakyomicin E.

The customary process steps can be used to isolate pure sakyomicin E, such as chromatography, gel filtration or precipitation from its solutions in suitable organic solvents. Chromatography on silica gel has proven particularly suitable, using as mobile phase a mixture of a lower alcohol and of a halogenated hydrocarbon, for example chloroform/methanol in the ratio 9:1 by volume, followed by HPLC separation on a reversed phase C-18 column with an isocratic mobile phase or a gradient of a lower alcohol and water, for example methanol/water in the ratio 1:1 (v/v) or acetonitrile and water in the ratio 2:3 (v/v) or a gradient which runs from 100% to 0% water, preferably 40%, continuously to 100% of the organic solvent with a rate of rise of 1 to 10% per minute, preferably 2% per minute. The sakyomicin E is then obtained from the appropriate fraction by evaporation of the organic component from the mobile phase or with the addition of 50% water and subsequent extraction with an organic solvent, for example ethyl acetate, and subsequent precipitation, for example by adding a concentrated solution of sakyomicin E dropwise to a nonpolar solvent, especially a hydrocarbon such as n-hexane or petroleum ether.

Sakyomicin E is a red amorphous solid which is readily soluble in ethyl acetate, methanol, acetone, DMSO and chloroform but is insoluble or only very slightly soluble in alkanes. The substance is stable in the solid state as well as in solution in the pH range from 3 to 9, especially from 5 to 8, and can thus be incorporated in customary pharmaceutical compositions.

Sakyomicin E exhibits an antibacterial effect against Gram-positive and Gram-negative bacteria which can be measured in vitro, for example in the agar plate diffusion test (10 μl/test disk 6 mm in diameter). Examples of various organisms which emerge as sensitive to an inhibitory concentration of greater than 10 μg/ml are: $E.\ coli,\ Staph.\ aureus,\ Strep.\ faecalis$.

The tumor-inhibiting effect of sakyomicin E has been shown in vitro on human and animal tumor cells.

Sakyomicin E is converted into the corresponding ($C_1$-$C_{18}$)-acyl compounds, preferably ($C_1$-$C_{10}$)-acyl compounds, especially the acetyl compounds, in a manner known per se using an acylating agent which introduces the desired acyl radicals of an organic carboxylic acid. Used for this purpose is the appropriate carboxylic acid or a reactive derivative, especially an anhydride. The acylation can be carried out in the presence of suitable condensing agents, for example in the presence of carbodiimide compounds such as dicyclohexylcarbodiimide or carbonyl compounds such as carbonyldiimidazole when free carboxylic acids are used, and, for example, in the presence of basic agents such as tri-lower-alkylamine, for example triethylamine, or heterocyclic bases, for example pyridine or 4-dimethylaminopyridine, or basic salts, for example anhydrous sodium acetate, when reactive carboxylic acid derivatives are used. The acylation reaction can be carried out in the absence or in the presence of a solvent or solvent mixture, with cooling, at room temperature, or with heating, and, if necessary, in a closed vessel and/or in an atmosphere of inert gas, for example nitrogen. Examples of suitable solvents are simple or substituted, for example chlorinated, aliphatic, cycloaliphatic or aromatic hydrocarbons, it being possible to use suitable esterifying agents such as acetic anhydride, but also suitable bases such as pyridine, as diluent.

However, the reaction is preferably carried out with an anhydride, especially acetic anhydride, in the presence of pyridine or sodium acetate. The reaction temperatures and reaction times are between $-10°$ and $100°$ C. and 2 minutes and 48 hours, preferably between $20°$ and $30°$ C. and 8 minutes and 16 hours. The ratio of anhydride to the base is in the range from 20:1 to 1:1, preferably 2:1. The concentration of sakyomicin E in the reaction mixture is between 0.05 to 10%, preferably 0.1 to 1%.

After the reaction is complete, the reaction product can be isolated by extraction. For further purification it is then chromatographed, for example, on silica gel.

Alternatively, mono- and diacyl compounds can be prepared by basic cleavage of 2,8,4'-tri-O-acyl-sakyomicin E. Bases such as the alkali metal and alkaline earth metal hydroxides or alkali metal carbonates are used in aqueous/alcoholic solution at $-10°$ to $100°$ C. The acyl cleavage is preferably carried out with a saturated sodium carbonate solution in aqueous/methanolic solution at $25°$ C. The subsequent working up is carried out as mentioned above.

The said acyl compounds are derived from organic carboxylic acids. These contain straight-chain, branched or cyclic aliphatic, aliphatic-aromatic or aromatic hydrocarbon radicals which are unsubstituted or substituted by a halogen, for example chlorine or bromine, or esterified or etherified hydroxyl groups.

The compounds prepared in this way likewise exhibit a tumor-inhibiting effect.

The invention is explained by means of examples hereinafter. Unless otherwise indicated, percentage data relate to weight.

EXAMPLES

Description of the Strain DSM 4249

Morphological Characteristics

The studies by Shirling, E. B. and Gottlieb, D.: Methods for characterization of Streptomyces species, Int. J. Systm. Bacteriol. 16, 313–340, 1966, were used for the assessments. The examinations for the optical and electron microscopy were carried out on a 14-day old culture.

Physiological Characteristics

| Carbohydrate utilization | |
| --- | --- |
| Glycerol | +/− |
| D - Xylose | + |
| Lactose | − |
| D - Fructose | + |
| L - Rham nose | + |
| Maltose | − |

-continued

| Carbohydrate utilization | |
|---|---|
| Inulin | + |
| Inositol | + |
| Raffinose | + |
| D - Galactose | + |
| L - Arabinose | + |
| Mannitol | + |
| D - Mannose | + |
| Sucrose | − |
| Cleavage of urea | |
| Urease activity | + |
| Melanin formation | − |
| Nitrate reduction | − |
| Hemolytic activity | − |

(1a) Preparation of a suspension of spores of the producer strain

Composition of the Preculture Medium

| Soybean peptone | 10 g |
|---|---|
| Glucose | 20 g |
| CaCO$_3$ | 2 g |
| CoCl$_2$.6 H$_2$O | 1 mg |
| Tap water | 1 l |
| pH (after autoclaving) | 7.2 |

Composition of the Agar

| Glucose | 20 g |
|---|---|
| Malt extract | 10 g |
| Yeast extract | 4 g |
| CaCO$_3$ | 2 g |
| Agar | 12 g |
| Tap water | 1 l |
| pH | 7.2 |
| (25 ml of nutrient solution/9 cm diameter Petri dish) | |

(b) Preparation of a Culture or of a Preculture of the Producer Strain in Erlenmeyer Flasks A 1000 ml Erlenmeyer flask containing 300 ml nutrient solution (described under preculture medium) is inoculated with 6 ml of the spore suspension and incubated in a shaker at 200 rpm and +27° C.

Sakyomicins are detectable after about 50 hours. Optimal sakyomicin E production is achieved by addition of 200 mg/l of the amino acid methionine and after about 60 hours.

(c) Preparation of a fermenter preculture 500 ml Erlenmeyer flask containing 100 ml of nutrient solution (described under preculture medium) is inoculated with spore material from an agar plate and incubated in an incubation shaker at 200 rpm and +27° C. for 72 hours.

2. Preparation of Sakyomicin E

Composition of the fermenter medium

| Soybean peptone | 10 g |
|---|---|
| Glucose | 20 g |
| CaCO$_3$ | 2 g |
| CoCl$_2$.6 H$_2$O | 1 mg |
| Methionine | 200 mg |
| Tap water | 1 l |
| pH (after autoclaving) | 7.2 |

A 10 l fermenter is operated under the following conditions:

| Incubation time | 72–96 hours |
|---|---|
| Incubation temperature | +27° C. |
| Stirring speed | 200–300 rpm |
| Aeration | submerged 300–400 l/h. |

TABLE 1

| Medium | Aerial mycelium | Growth | Substrate mycelium | Soluble pigment |
|---|---|---|---|---|
| Glucose/yeast extract/malt extract agar | white (with gray luster) | +++ | dark red | + (dark red) |
| Glycerol/asparagine agar | yellowish white | +++ | brownish red | + (brownish red) |
| Starch/mineral salt agar | white, sparsely developed | ++ | beige | − (pale pink) |
| Glycerol/glycine agar | white/gray | +++ | beige/red | + (dark red) |
| Glycerol/starch/glutamate agar | flinty gray | +++ | red/brown | + (violet) |
| Potato/carrot agar | white | +++ | beige | − |
| Malt extract agar | white/gray | +++ | red | + (orange-red) |
| Casein/starch/peptone/yeast extract agar | white, sparsely developed | ++ | beige | − (pale pink) |
| Czapek peptone/yeast agar | gray/white, sparsely developed | ++ | beige | − (pale pink) |

200 ml of nutrient solution of the preculture medium in an Erlenmeyer flask are inoculated with the strain DSM 4249 and incubated in a rotary shaker at 200 rpm and +27° C. for 68 hours. Then 1 ml of culture liquid is uniformly distributed on the nutrient medium and incubated and +27° C. for 14 days. The spores which have been produced after this time on one agar plate are removed with a glass spatula and homogenized in a glass mortar (Braun Melsungen) with the addition of 12 ml of physiological NaCl.

The formation of foam can be suppressed by repeated addition of a few drops of polypropylene glycol. The production maximum is at about 80 hours. The pH is about 7.8 at the end. The yields are about 1.7 g of crude extract/10 l of culture broth.

3. Isolation of sakyomicin E

After the fermentation of the strain DSM 4249, the culture broth is filtered with the addition of 2% Celite as filtration aid. The mycelium is extracted with acetone, the organic phase is evaporated, and the aqueous residue is extracted with ethyl acetate. The culture filtrate is likewise extracted exhaustively with ethyl acetate at pH 7.5. This extract is combined with the mycelium (or worked up separately), dried and evaporated. The oily residue is taken up in a little chloroform and added dropwise to a large quantity of petroleum ether or n-hexane. The precipitate which has separated out is removed by centrifugation and dried. The crude product is purified on a silica gel column (®LiChroprep Si100, 25–40 μm, from Merck) using chloroform/methanol (9:1 v/v). Sakyomicin E was concentrated in fractions 3 and 4 (red) of the eluate. It was subsequently purified by HPLC on RP-18 columns using methanol/water 1:1.

4. Purification of Sakyomicin E

Sakyomicin E is purified to a more than 98% purity by reversed phase HPLC. For this purpose, 60 mg are applied to a semipreparative Nucleosil 7 C18 HPLC column from Macherey & Nagel, FRG, and eluted with 50% methanol/water. The flow rate is 9 ml/min. A UV detector at a wavelength of 260 nm is used for detection. Water (about 50%) is added to the appropriate fraction. It is then extracted with ethyl acetate, once with the same volume and subsequently twice with half the volume. After drying with $Na_2SO_4$, the organic solvent is evaporated off in vacuo. Pure crystalline sakyomicin E is obtained by taking up in a small amount of chloroform and precipitation in n-hexane.

5. Characterization of Sakyomicin E

The physicochemical properties of the antibiotic sakyomicin E isolated as in Example 3 are as follows:

Thin-layer chromatography (silica gel 60 F254 aluminum sheet from Merck, and Alugram Sil G from Macherey & Nagel):

|  | Merck | Macherey & Nagel |
| --- | --- | --- |
| Chloroform/methanol (9:1) | Rf 0.34 | Rf 0.49 |
| Benzene/methanol (8:2) | Rf 0.32 | Rf 0.43 |
| Ethyl acetate/methanol (98:2) | Rf 0.42 | Rf 0.54 |
| Dichloromethane/ethanol (9:1) | Rf 0.48 | Rf 0.56 |

Figure 1:
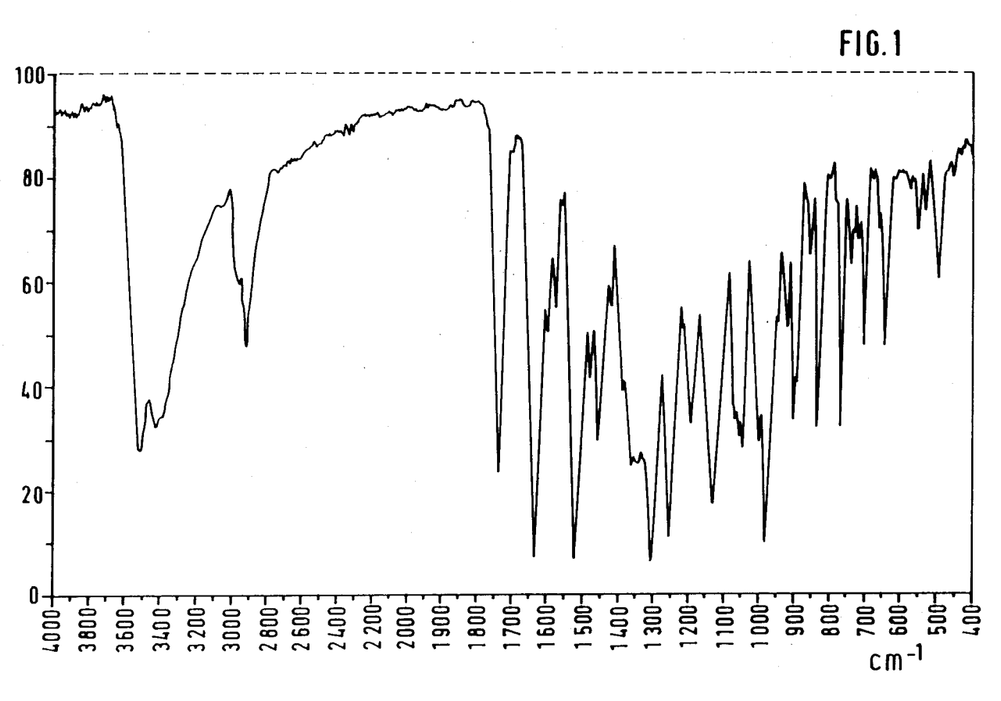
Figure 2:
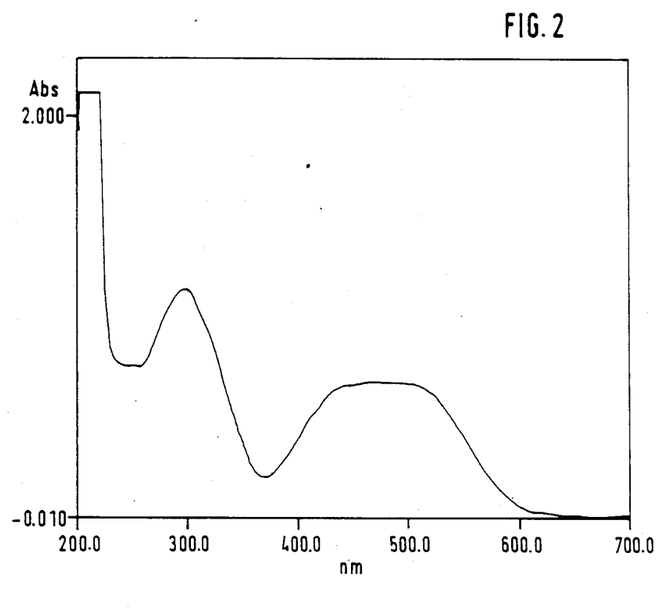
Figure 3:
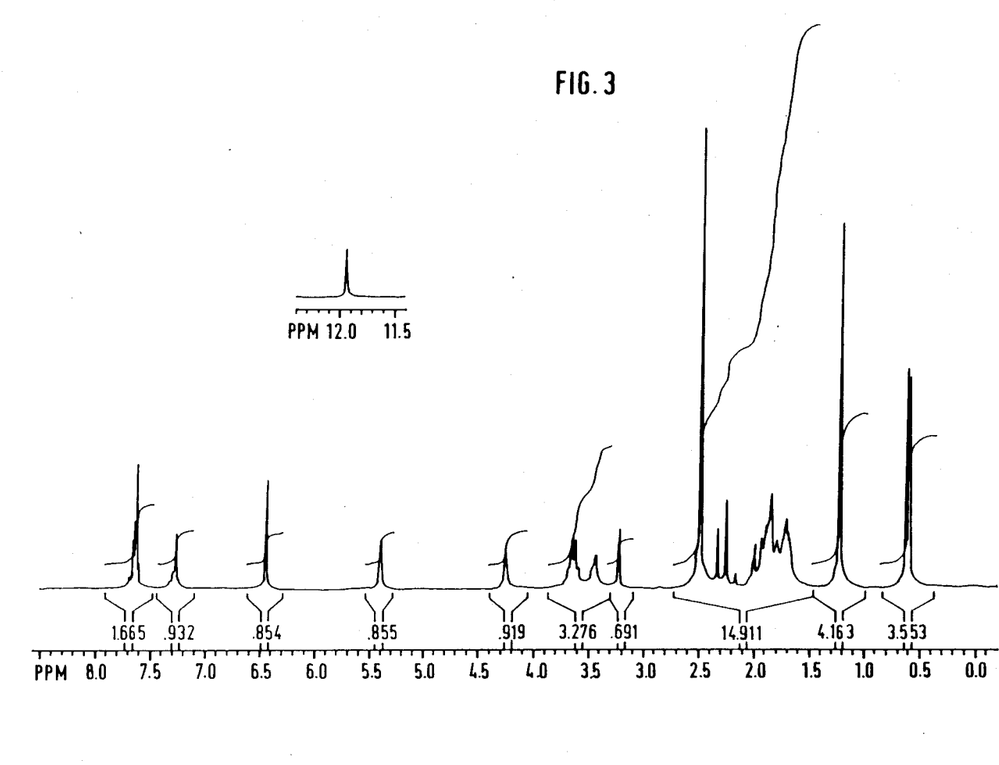

$C_{26}H_{28}O_{10}$ (MW 532.57)
Melting point: 204° C.
IR (KBr disk): FIG. 1
UV (in methanol): FIG. 2
$^1$H NMR (200 MHz, $CDCl_3$): FIG. 3

Figure 4:
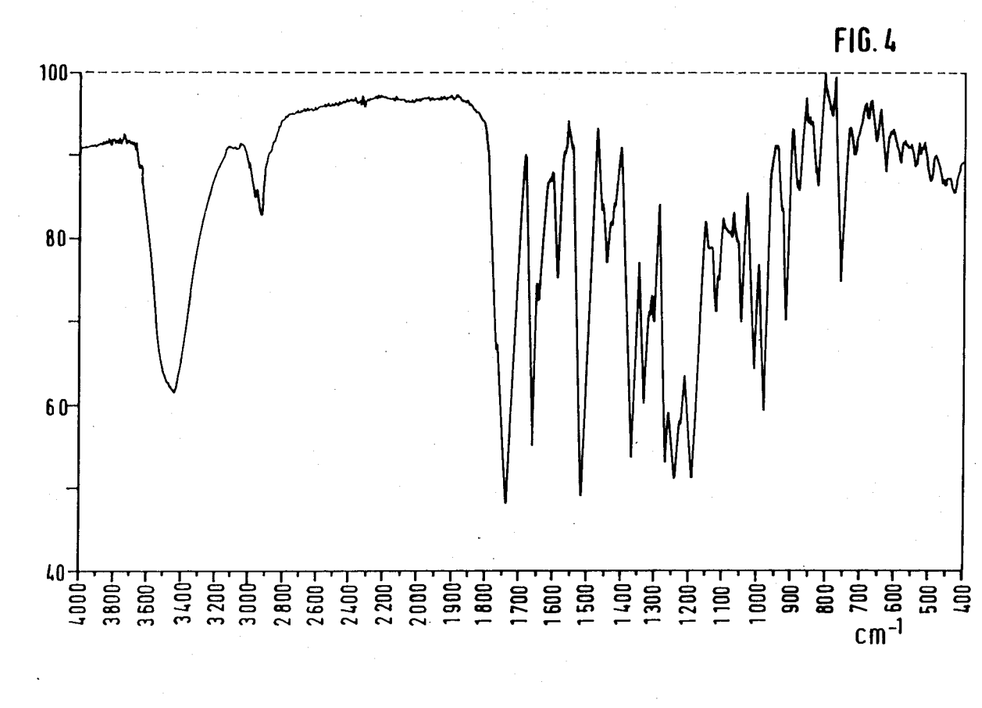
Figure 5:
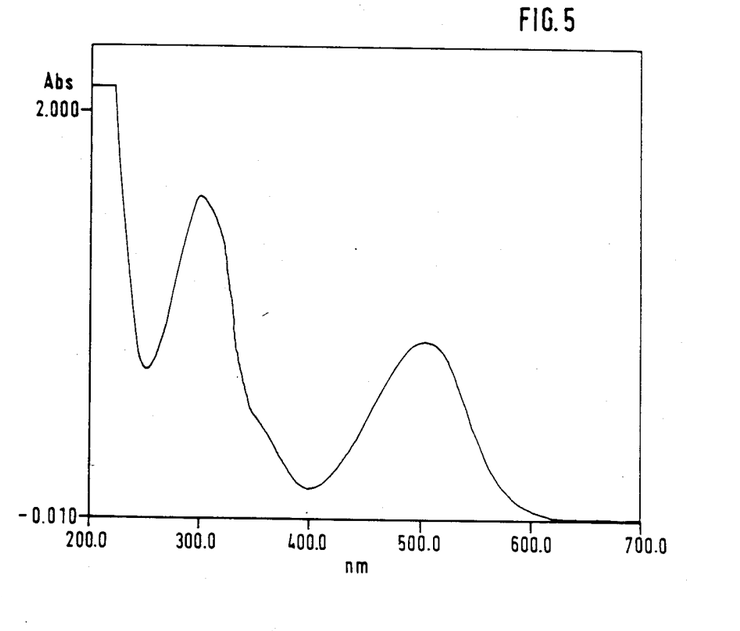
Figure 6:
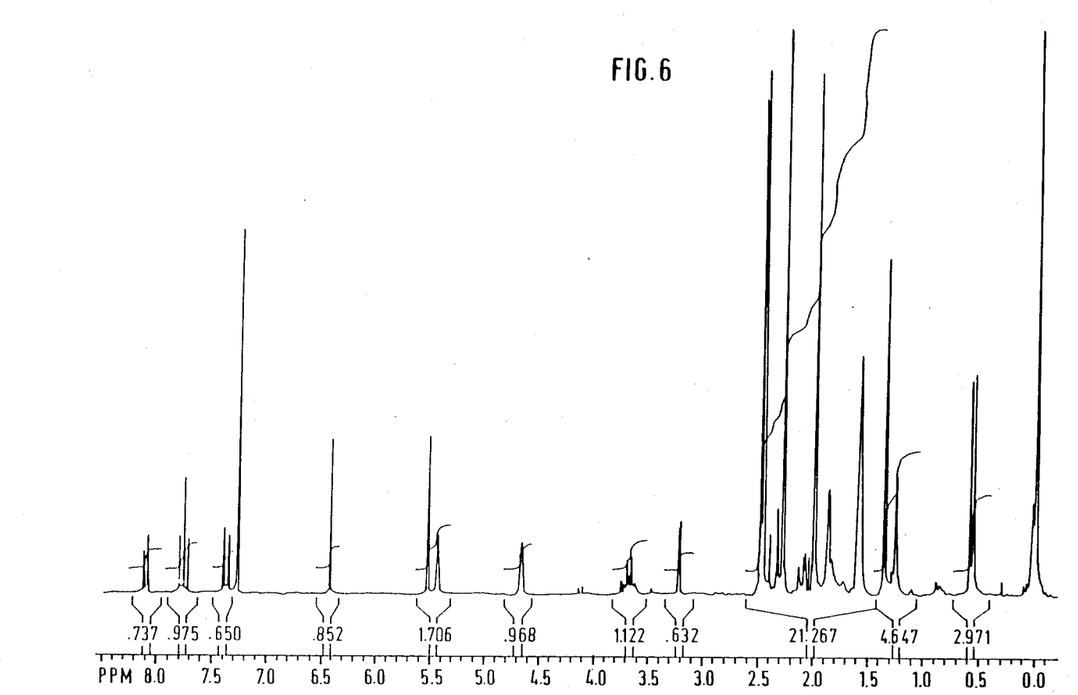

6. Preparation of 2,8,4'-tri-O-acetylsakyomicin E 40 mg of sakyomicin E are stirred in 40 ml of an acetic anhydride/pyridine mixture (2:1, v/v) at room temperature for 17 hours. The mixture is poured into ice-water (about 10 ml) and extracted twice with 20 ml of chloroform. The organic phase is concentrated in vacuo, and the remaining pyridine is removed by taking up and evaporating with toluene several times. The residue is chromatographed on silica gel 60 (preparative TLC silica gel 60, layer thickness 0.5 mm, from Merck) in the mobile phase chloroform/acetone (10:3 v/v). Two main bands are obtained.
1. Upper red band (Rf=0.62) tetra-O-acetyl-sakyomicin E 8 mg
2. Lower red band (Rf=0.38) tri-O-acetyl-sakyomicin E 42 mg $C_{32}H_{34}O_{13}$ (MW 658.68)
Melting point: 177° C.
IR (KBr disk): FIG. 4
UV (in methanol): FIG. 5
$^1$NMR (200 MHz, $CDCl_3$) FIG. 6

7. In vitro testing for cytotoxic activity

The cytotoxic activity of the compounds according to the invention was measured in two different in vitro test systems.

1. Proliferation test (MTT assay)

In this test system, the number of live or dead cells after incubation with the test substance for 3 days is measured by means of the NADP-dependent reduction of a colorless substrate to give a deep red-colored final product, which occurs only in live cells.

L1210, A 549 or HT 29 in the exponential phase of growth are incubated at a cell density of $5 \times 10^3$ cells/ml in RPMI 1640 in a 96-well micrometer plate with various concentrations of the test substance at 37° C., 5% $CO_2$ and 95% relative humidity for 72 hours. Control experiments contain merely growth medium in place of the test substance. Quadruplicate determinations were set up for each test substance and for the controls. After incubation for 65 hours, 50 μl of an MTT solution (2.5 mg/ml in phosphate buffered saline) are added. In the presence of live cells MTT is reduced to a dark-red insoluble formazan pigment. This reaction is complete after 7 hours (L1210 cells) or after 24 hours (A 549, HT 29 cells), and the supernatant medium is carefully removed by aspiration. The insoluble pigment is dissolved by addition of 100 μl of DMSO, and the extinction of the solution produced in this way is subsequently measured for each well in a Multiscan photometer 340 CC from Flow at a wavelength of 492 nm.

The ratio of the extinctions for treated and untreated cells yields a dose-effect plot from which it is possible to read off the concentration which just kills 50% of the cells ($IC_{50}$). The coefficient of variation for repeat investigations is less than 15%. The results are compiled in Table 1.

2. Stem Cell Test

This test system examines the ability of the test substance to inhibit the formation of tumor cell colonies in soft agar. The test was carried out by the method described by Hamburger and Salmon, with the modifications described below. Conditioned medium was replaced by McCoy 5A medium. As a consequence of the high cloning rate of the cell lines in soft agar, the number of tumor cells per plate was reduced to $5 \times 10^2$ (L1210) or $5 \times 10^3$ (A 549, HT 29). The cells were incubated with various concentrations of the test substance at 37° C. for 1 hour. The cells were then washed twice with McCoy 5A medium and then plated out as the upper layer in a two-layer agar system in accordance with the Hamburger and Salmon method. Additional parallel experiments were carried out using a continuous incubation time, in which case various concentrations of the test substance were mixed with the upper agar layer before plating out the cells.

The plates were incubated in an incubator with 5% $CO_2$, 20% $O_2$ and 95% relative humidity for 5–7 days (L1210) or 14 days (A 549, HT 29). After this time, colonies with a diameter of (greater than) 60 μm were counted using an image analysis system (FAS II, Bausch and Lomb).

The results have been reported as percentage colonies in treated versus untreated groups. The coefficient of variation for repeat experiments was less than 15%. The IC$_{50}$ for continuous and one-hour incubation was determined from the dose-effect plot (Tab. 2).

The data show that the two compounds have high cytotoxicity for various human (A 549, HT 29) and murine (L1210) cell lines.

TABLE 2

|  | IC$_{50}$ (µg/ml) | | |
| --- | --- | --- | --- |
|  | L1210 | A 549 | HT 29 |
| Sakyomicin E | 0.50 | 0.30 | 0.08 |
| 2,8,4'-Tri-O-acetylsakyomicin E | 0.29 | 0.37 | 0.11 |

TABLE 3

|  | IC$_{50}$ (µg/ml) | |
| --- | --- | --- |
|  | Cont. incubation | 1 h incubation |
| Sakyomicin E | 0.24 | 3.0 |
| 2,8,4'-Tri-O-acetylsakyomicin E | 0.30 | above 1.0 |

We claim:
1. A compound of the formula I in which R$_1$ to R$_3$ denote, independently of one another, hydrogen or a (C$_1$-C$_{18}$)-acyl group.

2. A compound as claimed in claim 1, in which R$_1$ to R$_3$ denote, independently of one another, hydrogen or acetyl, with at least one R being acetyl.

3. A medicinal composition comprising a compound as claimed in claim 1 and suitable pharmaceutical carrier.

* * * * *